United States Patent
Shen et al.

(10) Patent No.: US 10,471,174 B2
(45) Date of Patent: Nov. 12, 2019

(54) CYANOACRYLATE MEDICAL ADHESIVE AND PREPARATION METHOD AND USE THEREOF

(71) Applicant: Wei Shen, Beijing (CN)

(72) Inventors: Wei Shen, Beijing (CN); Jinghai Xu, Beijing (CN); Shufang Yu, Beijing (CN); Pengfei Wang, Beijing (CN); Jie Shao, Beijing (CN)

(73) Assignee: Wei Shen, Beijing (CN)

( * ) Notice: Subject to any disclaimer, the term of this patent is extended or adjusted under 35 U.S.C. 154(b) by 20 days.

(21) Appl. No.: 15/751,986

(22) PCT Filed: Aug. 19, 2015

(86) PCT No.: PCT/CN2015/087551
§ 371 (c)(1),
(2) Date: Feb. 12, 2018

(87) PCT Pub. No.: WO2017/024606
PCT Pub. Date: Feb. 16, 2017

(65) Prior Publication Data
US 2019/0175782 A1    Jun. 13, 2019

(30) Foreign Application Priority Data
Aug. 11, 2015 (CN) .......................... 2015 1 0489872

(51) Int. Cl.
| | |
|---|---|
| *A61L 24/06* | (2006.01) |
| *A61L 24/04* | (2006.01) |
| *C09J 133/14* | (2006.01) |
| *A61L 24/00* | (2006.01) |

(52) U.S. Cl.
CPC .......... *A61L 24/043* (2013.01); *A61L 24/001* (2013.01); *A61L 24/0042* (2013.01); *A61L 24/0094* (2013.01); *A61L 24/06* (2013.01); *C09J 133/14* (2013.01)

(58) Field of Classification Search
CPC .................................................. A61L 24/06
See application file for complete search history.

(56) References Cited

U.S. PATENT DOCUMENTS

| | | | |
|---|---|---|---|
| 2003/0037310 A1 | 2/2003 | Ge | |
| 2003/0082116 A1* | 5/2003 | Badejo | ................. A61K 36/185 424/58 |
| 2009/0326095 A1* | 12/2009 | Badejo | .................... A61L 15/58 523/118 |

FOREIGN PATENT DOCUMENTS

| | | |
|---|---|---|
| CN | 101495377 | 7/2009 |
| CN | 103083718 | 5/2013 |
| CN | 103585671 | 2/2014 |
| CN | 104520396 | 4/2015 |
| CN | 104710953 | 6/2015 |
| WO | WO 02/09785 | 2/2002 |
| WO | WO 2014/085592 | 6/2014 |
| WO | WO 2015/059644 | 4/2015 |

OTHER PUBLICATIONS

International Search Report dated May 11, 2016 with English translation from corresponding application No. PCT/CN2015/087551.
Written Opinion dated May 11, 2016 with English translation from corresponding application No. PCT/CN2015/087551.
First Office Action dated May 4, 2017 with English translation from corresponding application No. CN201510489872.3.
Notification of Decision to Grant Patent Right for Invention dated Oct. 30, 2017 with English translation from corresponding application No. CN201510489872.3. (Includes granted publication and English translation of the granted claims.
First search with English translation from corresponding application No. CN201510489872.3.

\* cited by examiner

*Primary Examiner* — Michael F Pepitone
(74) *Attorney, Agent, or Firm* — Hauptman Ham, LLP

(57) ABSTRACT

The invention relates to a novel cyanoacrylate medical adhesive and preparation method and application thereof, the main components of the medical adhesive is composed of alkyl cyanoacrylate and/or alkoxy cyanoacrylate and lactyl cyanoacrylate, and by adding a novel stabilizer system, the stability of the novel cyanoacrylate medical adhesive product in the invention increases substantially, the product can be stored and transported at room temperature, degradation performance of the product was greatly improved, the main technical indicators of product such as curing time and mechanical properties can meet the clinical needs, and the user experience of the product such as adhesive film flexibility is greatly improved, so the cyanoacrylate medical adhesive is an widely used surgical hemostatic materials.

19 Claims, No Drawings

CYANOACRYLATE MEDICAL ADHESIVE AND PREPARATION METHOD AND USE THEREOF

CROSS-REFERENCE TO RELATED APPLICATIONS

This present application is a National Phase of International Application Number PCT/CN2015/087551, filed Aug. 19, 2015, and claims the priority of China Application No. 201510489872.3, filed Aug. 11, 2015, the disclosures of which are incorporated herein by reference.

TECHNICAL FIELD

The invention belongs to the technical field of biological material, and particularly relates to novel cyanoacrylate medical adhesive, preparation method and use thereof. Cyanoacrylate medical adhesive of the invention can be stored for a long time at room temperature, and can achieve rapid degradation and excellent user experience.

BACKGROUND TECHNOLOGY

According to statistics, more than 4 million cases of surgery are performed every year in the world. The hemostasis and antisepsis of the wound are key operations in surgery, especially when the operation need sew and ligate for repairing the tissue of organism. However, the operation is not only tedious, laborious, time-consuming, but also easy to cause new damage, bleeding and bring about more pain to the patient. For large areas of bleeding in which bleeding spots can't be found, doctors feel helpless, while the emergence of medical adhesive with fast hemostasis, sealing and adhesion functions provides a solution for solving the above problems.

Medical adhesive generally refers to the cyanoacrylate tissue adhesive, which mechanism of action is thought of as anions polymerization in presence of trace anions in wound blood and tissue fluid, and the resulted elastic thin adhesive film which shows high tensile strength. The adhesive film is observed as a network structure under electron microscope, which can effectively block the hemoglobin and platelet to achieve desired effect of hemostasis, adhesion and sealing. First cyanoacrylate adhesive on reported can be traced back to 1959, methyl cyanoacrylate (Eastman910) was developed by the United States Eastman Kodak company, and the product immediately attracted the attention of the medical profession for its instant adhesive property. Later homologous series of cyanoacrylate were synthesized including the ethyl cyanoacrylate, n-butyl cyanoacrylate, n-octyl cyanoacrylate, ethoxy ethyl cyanoacrylate, ethoxy butyl cyanoacrylate, ethoxy octyl cyanoacrylate, butyl lactyl cyanoacrylate, isooctyl lactyl cyanoacrylate etc. Cyanoacrylate adhesive shows some advantages, such as simple composition, easy use, fast solidification at room temperature, and high bonding strength, so it can be applied in many fields including the medical field. The cyanoacrylate medical adhesive has been widely used in clinic, including the main use field of adherence of incisions and wounds on the body surface, closed hemostasis of the body organ section as well as esophageal and fundal varices and vascular embolization.

The chemical structure of cyanoacrylate compounds commercially available at present can be expressed by formula I:

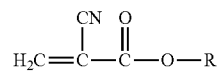

(formula I)

1) R can be a linear, branched or cyclic alkyl group with 1-20 carbon atoms;

or, 2) R can also be a group of formula $-R_2-O-R_3$, in which $R_2$ and $R_3$ are linear, branched or cyclic alkyl groups with 1-20 carbon atoms respectively and independently.

or, 3) R can be a group of formula $-R_4-COO-R_5$, in which $R_4$ and $R_5$ are linear, branched or cyclic alkyl groups with 1-20 carbon atoms respectively and independently.

According to different ester parts, the formula I cyanoacrylate compound can be divided into: 1) alkyl cyanoacrylate; 2) alkoxy cyanoacrylate; 3)lactyl cyanoacrylate. Alkyl cyanoacrylate and alkoxy cyanoacrylate products have the advantages of fast bonding rate and high bonding strength, but in clinical applications especially in vivo applications, these two products have their own shortcomings, namely the stable chemical property of formed polymer and the deficiency of enzymes for effectively decomposing the polymer, which lead to these two kinds of polymer present in the body for a long time as a foreign body (or implants) and bring some risk to the patient. The alkyl cyanoacrylate product also has the disadvantage of hard adhesive film. Compared with alkyl cyanoacrylate and alkoxy cyanoacrylate, lactyl cyanoacrylate product is better in degradation and biological compatibility, especially faster in degradation rate, and more secure in vivo medical uses, while the bonding rate and bonding strength of lactyl cyanoacrylate have weakness.

In order to improve the degradation rate of alkyl cyanoacrylate, scientists both at home and abroad have done a lot of attempts. For example, the alkyl cyanoacrylate and lactyl cyanoacrylate were mixed in a certain proportion, and two monomers were copolymerized in situ to form copolymers in practical application. Because polymer fragment of the lactyl cyanoacrylate provides a degradable part for copolymer, the degradation rate of the copolymer was greatly improved, and due to more excellent biocompatibility of lactyl cyanoacrylate, the product not only provides high bonding strength and good degradation rate, but also brings a better user experience. However, lactyl cyanoacrylate is very unstable, and is sensitive to acid and alkali and prone to hydrolysis for its lactyl structure, and hydrolysis products can further accelerate the polymerization of lactyl cyanoacrylate, so these products are very difficult to store for a long time at room temperature. Although low temperature facilities can be used to extend the storage period of lactyl cyanoacrylate medical adhesive, it will greatly increase the cost of production, storage and transportation, and will also bring additional risks.

To sum up, the prior arts of cyanoacrylate medical adhesive have defects, in clinical, medical adhesive with the features of a long-term storage, a rapid degradation rate, a rapid bonding rate, excellent bonding strength and excellent softness of adhesive film is needed. The purpose of the present disclosure is to provide cyanoacrylate medical adhesive which can be stored for a long time and has the features of a rapid degradation rate, a rapid bonding rate, excellent bond strength and softness of adhesive film.

CONTENT OF THE INVENTION

Technical Problems to be Solved

The purpose of the present disclosure is to provide cyanoacrylate medical adhesive which can be stored for a long-term at room temperature and degrade rapidly in vivo.

Another purpose of the present disclosure is to provide a method for preparing the cyanoacrylate medical adhesive.

Another purpose of the present disclosure is to provide a use of the cyanoacrylate medical adhesive as a hemostatic material.

Technical Solution

The disclosure is realized by the following technical solutions:

Cyanoacrylate medical adhesive, wherein the medical adhesive is prepared by raw materials comprising the following components: a cyanoacrylate composition (A); and a composite stabilizer (C);

wherein the cyanoacrylate composition (A) comprises the following components:

A1: a alkyl cyanoacrylate compound and/or alkoxy cyanoacrylate compound, wherein the alkyl cyanoacrylate compound comprises one or more compounds of methyl cyanoacrylate, ethyl cyanoacrylate, isobutyl cyanoacrylate, n-butyl cyanoacrylate, n-octyl cyanoacrylate, or isooctyl cyanoacrylate etc.; the alkoxy cyanoacrylate compound comprises one or more compounds of methoxy methyl cyanoacrylate, methoxy ethyl cyanoacrylate, methoxy butyl cyanoacrylate, methoxy octyl cyanoacrylate, ethoxy methyl cyanoacrylate, ethoxy ethyl cyanoacrylate, ethoxy butyl cyanoacrylate, or ethoxy octyl cyanoacrylate; and A2: a lactyl cyanoacrylate compound, wherein the lactyl cyanoacrylate compound comprises one or more compounds of methyl lactyl cyanoacrylate, ethyl lactyl cyanoacrylate, propyl lactyl cyanoacrylate, butyl lactyl cyanoacrylate, pentyl lactyl cyanoacrylate, hexyl lactyl cyanoacrylate or isooctyl lactyl cyanoacrylate.

The composite stabilizer (C), which comprises at least the following components:

C1: an anion polymerization inhibitor, which comprises a strong acid substance selected from perchloric acid, permanganic acid, sulfuric acid, methanesulfonic acid, p-toluene sulfonic acid, hydrofluoric acid, sulfonic acid or their compositions;

C2: a gas polymerization inhibitor, which is strong acid gas selected from hydrogen chloride, boron trifluoride, sulfur dioxide, nitrogen dioxide or their compositions.

C3: a free radical polymerization inhibitor, which comprises a quinone polymerization inhibitor with smaller steric hindrance and a quinone polymerization inhibitor with larger steric hindrance. The quinone polymerization inhibitor with smaller steric hindrance comprises one or more compounds of hydroquinone, p-hydroxyanisole and p-dimethoxybenzene; the quinone polymerization inhibitor with larger steric hindrance comprises one or more compounds of butyl hydroxyanisole (BHA), 2,6-di-tert-butyl-4-methylphenol(BHT), tert-butyl hydroquinone(TBHQ), 2,5-di-tert-butyl hydroquinone(DBHQ), p-tert-butylcatechol (TBC), 1,1-diphenyl-2-trinitrophenyl hydrazine(DPPH);

C4: a natural antioxidant, which is selected from phytic acid, citric acid and ascorbic acid.

According to a preferred embodiment of the disclosure, the degradable cyanoacrylate medical adhesive comprises degradable polymer (B), wherein B is at least one kind of degradable polymer selected from polylactide (PGA), polylactic acid (PLA), polycaprolactone (PCL), copolymer of lactic acid and lactide (PLGA) and copolymer of lactic acid and caprolactone (PLCL).

According to another preferred embodiment of the disclosure, the alkyl cyanoacrylate compound is preferably n-butyl cyanoacrylate or isooctyl cyanoacrylate; the alkoxy cyanoacrylate compound is preferably ethoxy ethyl cyanoacrylate.

According to another preferred embodiment of the disclosure, the lactyl cyanoacrylate compound is preferably butyl lactyl cyanoacrylate(BLCA) or isooctyl lactyl cyanoacrylate.

According to another embodiment of the present disclosure, the degradable polymer (B) is preferably polylactic acid (PLA) or copolymer of lactic acid and lactide (PLGA).

According to another embodiment of the present disclosure, the anion polymerization inhibitor is preferably methanesulfonic acid or p-toluene sulfonic acid.

According to another embodiment of the present invention, the gas polymerization inhibitor is preferably sulfur dioxide or boron trifluoride.

According to another embodiment of the present disclosure, the quinone polymerization inhibitor with smaller steric hindrance is preferably p-hydroxyanisole; the quinone polymerization inhibitor with larger steric hindrance is preferably butyl hydroxyanisole (BHA) or 2,5-di-tert-butyl hydroquinone (DBHQ).

According to another embodiment of the present disclosure, the natural antioxidant is preferably phytic acid.

According to another embodiment of the present disclosure, the molar ratio of alkyl cyanoacrylate compound and/or the alkoxy cyanoacrylate compound (A1) to lactyl cyanoacrylate compound (A2) is A1:A2=10:1-1:1; the mass ratio of cyanoacrylate composition (A) to the degradable polymer (B) is A:B=100:1-20:1.

According to another embodiment of the present disclosure, the anion polymerization inhibitor amount is preferably 30-1000 ppm of total weight of cyanoacrylate medical adhesive, more preferably 50-500 ppm of total weight of cyanoacrylate medical adhesive, and most preferably 50-200 ppm of total weight of cyanoacrylate medical adhesive.

According to another embodiment of the present disclosure, the gas polymerization inhibitor amount is preferably 20-500 ppm of total weight of cyanoacrylate medical adhesive, more preferably 30-300 ppm of total weight of cyanoacrylate medical adhesive, and most preferably 50-200 ppm of total weight of cyanoacrylate medical adhesive.

According to another embodiment of the present disclosure, the amount of the free radical polymerization inhibitor with smaller steric hindrance is preferably 50-2000 ppm of total weight of cyanoacrylate medical adhesive, more preferably 100-1000 ppm of total weight of cyanoacrylate medical adhesive, and most preferably 300-800 ppm of total weight of cyanoacrylate medical adhesive. The amount of the free radical polymerization inhibitor with larger steric hindrance is preferably 50-1000 ppm of total weight of cyanoacrylate medical adhesive, more preferably 100-800 ppm of total weight of cyanoacrylate medical adhesive, and most preferably 200-500 ppm of total weight of cyanoacrylate medical adhesive.

According to another embodiment of the present disclosure, the natural antioxidant amount is preferably 30-1000 ppm of total weight of cyanoacrylate medical adhesive, more preferably 50-500 ppm of total weight of cyanoacrylate medical adhesive, and most preferably 100-300 ppm of total weight of cyanoacrylate medical adhesive.

The amount of substance in the present disclosure is represented by "number ppm of total weight of cyanoacrylate medical adhesive", it means there is number*$10^{-6}$ g substance in 1 g cyanoacrylate medical adhesive, and for example, the natural antioxidant amount is more preferably 50-500 ppm of total weight of cyanoacrylate medical adhesive means each 1 g cyanoacrylate medical adhesive has $(50\text{-}500)*10^{-6}$ g natural antioxidant.

The present disclosure provides a method for preparing cyanoacrylate medical adhesive which is degradable and could be stored for a long time, and the preparation method comprises the following steps:

1) According to the formula, weighting successively prescribed amount of alkyl cyanoacrylate and/or alkoxy cyanoacrylate, lactyl cyanoacrylate, free radical polymerization inhibitor, anion polymerization inhibitor and natural antioxidant, mixing evenly to obtain colorless liquid;

2) Adding gas polymerization inhibitor to the colorless liquid obtained in step 1), then sealing well, and stirring for 12-24 hours at room temperature; and 3) Under the condition of local hundred class, filtering the mixture obtained in step 2 to remove bacteria and obtain sterile degradable cyanoacrylate medical adhesive.

Preferably, a degradable polymer is added in step 1).

The amount relationship of each component is described as above.

The present disclosure also provides a use of the degradable cyanoacrylate medical adhesive as a hemostatic material.

Beneficial Effect

Cyanoacrylate medical adhesive and preparation method thereof in the disclosure can obtain the following beneficial effects:

(1) Product stability is greatly improved, and the product can be stored and transported at room temperature and overcomes the technical problems that have not been solved for a long time in the prior art.

(2) The degradation rate of the product has been greatly improved, and the degradation test in vitro shows that the degradation time (37° C.) can be controlled within 90 days.

(3) The cyanoacrylate medical adhesive can be stored for a long time at room temperature and can degrade rapidly, at the same time it has outstanding technical indicators, such as rapid adhesion, excellent bonding strength, softness of adhesive film, which can well meet the clinical needs.

Specific Implementation Methods

The detailed implementation and specific operation process are given in the examples to help the understanding of the disclosure.

The methods used in the examples with no special description are conventional methods. In the disclosure, the detection of medical adhesive used the following detection methods:

1. Detection of Shelf Life ($TIME_{RT}$)

Sample preparation: according to the preparation method of the cyanoacrylate medical adhesive, sterile medical adhesive was prepared, and the sterile medical adhesive was encapsulated in the 1 mL ampoule bottle, of which filling volume is 0.5 mL.

The ampoule bottle containing the medical adhesive was transferred to a biological incubator with temperature of 55±1° C., the technical indicators of the medical adhesive were detected within prescribed time interval until the product was ineffective, and this time was the test time of the product ($TIME_{T1}$).

The relationship between the test time and shelf life is as follows:

$$TIME_{T1} = TIME_{RT}/Q10^{\wedge}[(T_{T1}-T_{RT})/10] \quad \text{(formula 1)}$$

In the formula: $T_{T1}$ was an accelerated aging temperature, the unit is centigrade (° C.), and the accelerated aging temperature of this test is 55° C.;

$T_{RT}$ was ambient temperature, the unit was centigrade (° C.), and the room temperature was selected in this test, that was 22° C.;

Q10 was an aging factor, and according to conservative calculation method of aging factor, Q10 was selected as 2.

The above data was brought into the formula 1:

$Q10[^{\wedge}(T_{T1}-T_{RT})/10]=2^{\wedge}[(55-22)/10]=2^{3.3}=9.9$, for convenience of calculation, Q10 was selected as 10.

The shelf life of medical adhesive in room temperature storage was calculated according to $$TIME_{55° C.} = TIME_{22° C.}/10 \quad \text{(formula 2)};$$

In the formula: $TIME_{RT}$ was the shelf life of medical adhesive in room temperature storage, for short as shelf life, and the unit was day(d);

$TIME_{T1}$ was the accelerated aging shelf life of medical adhesive, and the unit was day(d);

The shelf life ($TIME_{22° C.}$) could be calculated by bringing the accelerated aging shelf life ($TIME_{55° C.}$) into the formula 2. When the accelerated aging shelf life ($TIME_{55° C.}$) of medical adhesive exceeded 73 days, namely when the shelf life ($TIME_{22° C.}$) of medical adhesive exceeded 730 days, the accelerated aging test was stopped. The shelf life of medical adhesive was calculated as 730 days.

2. Detection of Curing Time (s):

0.3 g/L NaHCO3 solution was added to the watch glass. The medical adhesive was picked up with sucker and dropped down from the place 5 cm above the liquid surface, and timing was started at the same time until the medical adhesive cured film completely, and this time was curing time.

3. Detection of Bonding Properties:

The bonding properties comprise four parts: strength in lap shear by tension loading, strength in T-peel by tension loading, tension strength and wound closure strength, and in the disclosure, the bonding properties of the gel was tested according to the detection method in YY/T 0729-2009.

1) Preparation of the Samples to be Tested:

Pigskin on both sides of the pig's belly was selected, surface fatty layer was removed until the dermis exposed, then the dermis was washed, dried and cut into rectangle to be used, which was required as longer than 5 cm for length, 2.5±0.1 cm for width, less than 5 mm for thickness.

2) Detection of bonding properties: two pieces of pigskin were glued together with medical adhesive, and the bonding properties of the gel hemostat material were tested according to the detection method in YY/T 0729-2009.

4. Detection of In Vitro Degradation Time ($TD_{t0}$):

1) Preparation of the samples to be tested: the medical adhesive was applied evenly to the agar, then the film cured completely, and the adhesive film was removed carefully and cut into a 1 cm*1 cm square adhesive film.

2) Preparation of PBS buffer solution of pH 7.4.

3) the sample prepared in step 1) was put in a closed container with PBS buffer solution, and transferred to an incubator with a temperature of 55±1° C., the changes of sample in the buffer were observed until naked eyes could not distinguish, this time was recorded as the accelerated aging in vitro degradation time ($TD_{T1}$) of medical adhesive.

The relationship between accelerated aging in vitro degradation time and in vitro degradation time was as follows:

$$TD_{T1} = TD_{T0}/Q10^{\wedge}[(T_{T1}-T_{T0})/10] \quad \text{(formula 3)}$$

In the formula: $T_{T1}$ was the accelerated aging temperature, the unit is centigrade (° C.), and the accelerated aging temperature selected in this test is 55° C.;

$T_{T0}$ was the body temperature, the unit was centigrade (° C.), and 37° C. was selected in the test;

Q10 was an aging factor, according to conservative calculation method of aging factor, Q10 was selected as 2.

The above data was brought into the formula 3:

$$Q10^{[(T_{T1}-T_{T0})/10]}=2^{(55-37)/10}=2^{1.8}=3.5$$

The in vitro degradation time of product was calculated according to $$TD_{37°\,C.}=TD_{55°\,C.}*3.5 \qquad \text{(formula 4)};$$

The In vitro degradation time of the medical adhesive ($TIVD_{37°\,C.}$) could be calculated by bringing the measured accelerated aging degradation time ($TIVD_{55°\,C.}$) into formula 4.

Preparation Example 1: Preparation of Butyl Lactyl Cyanoacrylate

1) Preparation of Butyl Lactyl Cyanoacetate

Under the condition of water bath, the cyanoacetic acid (86 g, 1.01 mol, Sinopharm Chemical Reagent Co., Ltd.), butyl lactate (134 g, 0.92 mol, Meryer (Shanghai) Chemical Technology Co., Ltd.) and 4-dimethylaminopyridine (DMAP, 1 g, Sinopharm Chemical Reagent Co., Ltd.) were weighted and put in a flask with three necks, dichloromethane (500 mL. Sinopharm Chemical Reagent Co., Ltd.) was added, then dicyclohexylcarbodiimide (DCC, 208 g, 1.01 mol, Sinopharm Chemical Reagent Co., Ltd.) was added in batches, and the reaction mixture temperature should be not higher than 30° C., and after that, the reaction mixture was stirred overnight. The reaction mixture was filtered to remove white precipitates, and light yellow solution was obtained, then the solvent was removed to obtain the pale yellow liquid, and then the pale yellow liquid was further rectified under reduced pressure to obtain the butyl lactyl cyanoacetate (170.6 g, 0.75 mol, yield 81.6%).

2) Preparation of Butyl Lactyl Cyanoacrylate

The butyl lactyl cyanoacetate (150 g, 0.70 mol) prepared in the above steps and 1, 2-dichloroethane (200 ml, Sinopharm Chemical Reagent Co., Ltd.) were added in a flask with four necks, and heated to 65-70° C., the mixture of water solution of formaldehyde (36%, 45 g, 0.65 mol, Sinopharm Chemical Reagent Co., Ltd.) and piperidine (0.5 mL, Sinopharm Chemical Reagent Co., Ltd.) were dropped, and in the process of dropping, the reaction temperature was controlled as less than 80° C. After dropping, the reaction mixture was heated to reflux and the reaction was continued for 3 hours with stirring and without heating.

Dibutyl phthalate (100 mL, Sinopharm Chemical Reagent Co., Ltd.) was added as thermal conductive agent, water separator was installed and began to water diverse until the water in the system was not obvious, then the water diversion device was changed to distillation device, the residual solvent in the system was removed, hydroquinone (4 g, Sinopharm Chemical Reagent Co., Ltd.), p-toluenesulfonic acid (2 g, Sinopharm Chemical Reagent Co., Ltd.) and phosphorus pentoxide (4 g, Sinopharm Chemical Reagent Co., Ltd.) were added as an polymerization inhibitor, obtained mixtures were pyrolysed under high temperature and reduced pressure (pyrolysis temperature was at 180-210° C.) until pyrolysis completed, and 180 g crude sample of butyl lactyl cyanoacrylate were obtained.

Further, the crude sample of butyl lactyl cyanoacrylate was rectified under reduced pressure and colorless or yellowish liquid was obtained, which was pure product of butyl lactyl cyanoacrylate (105 g, yield 71.8%).

Preparation Example 2: Preparation of Isooctyl Lactyl Cyanoacrylate

1) Preparation of Isooctyl Lactyl Cyanoacetate

The isooctyl lactyl cyanoacetate was prepared according to the preparation method of butyl lactyl cyanoacetate, the feeding was as follows: cyanoacetic acid (86 g, 1.01 mol, Sinopharm Chemical Reagent Co., Ltd.), isooctyl lactate (186 g, 0.92 mol, Meryer (Shanghai) Chemical Technology Co., Ltd.), 4-dimethylaminopyridine (DMAP, 2 g, Sinopharm Chemical Reagent Co., Ltd.), dichloromethane (500 mL, Sinopharm Chemical Reagent Co., Ltd.), and dicyclohexylcarbodiimide (DCC, 208 g, 1.01 mol, Sinopharm Chemical Reagent Co., Ltd.), and then the mixture was rectified under reduced pressure to obtain isooctyl lactyl cyanoacetate (154 g, 0.57 mol, yield 62.2%).

2) Preparation of Isooctyl Lactyl Cyanoacrylate

The isooctyl lactyl cyanoacrylate was prepared according to the preparation method of butyl lactyl cyanoacrylate, the feeding was as follows: isooctyl lactyl cyanoacetate (100 g, 0.37 mol), 1,2-dichloroethane (200 ml, Sinopharm Chemical Reagent Co., Ltd.), water solution of formaldehyde (36%, 28.5 g, 0.34 mol, Sinopharm Chemical Reagent Co., Ltd.), piperidine (0.5 mL, Sinopharm Chemical Reagent Co., Ltd.), dibutyl phthalate (100 mL, Sinopharm Chemical Reagent Co., Ltd.), hydroquinone (4 g, Sinopharm Chemical Reagent Co., Ltd.), p-toluenesulfonic acid (3 g, Sinopharm Chemical Reagent Co., Ltd.), and phosphorus pentoxide (4 g, Sinopharm Chemical Reagent Co., Ltd.), then the pure isooctyl lactyl cyanoacrylate was obtained (62 g, 0.22 mol, yield 64.8%).

Preparation Example 3: Preparation of N-Butyl Cyanoacrylate

The n-butyl cyanoacrylate was prepared according to the preparation method of butyl lactyl cyanoacrylate, the feeding was as follows: n-butyl cyanoacetate (200 g, 1.42 mol, Tstachi (Shanghai) into Industrial Development Co., Ltd.), 1,2-dichloroethane (200 ml, Sinopharm Chemical Reagent Co., Ltd.), water solution of formaldehyde (36%, 109 g, 1.31 mol, Sinopharm Chemical Reagent Co., Ltd.), piperidine (1 mL, Sinopharm Chemical Reagent Co., Ltd.), dibutyl phthalate (150 mL, Sinopharm Chemical Reagent Co., Ltd.), hydroquinone (5 g, Sinopharm Chemical Reagent Co., Ltd.), p-toluenesulfonic acid (2.5 g, Sinopharm Chemical Reagent Co., Ltd.), and phosphorus pentoxide (5 g, Sinopharm Chemical Reagent Co., Ltd.), and then the pure isooctyl lactyl cyanoacrylate was obtained (145 g, 0.95 mol, yield 72.5%).

Preparation Example 4: Preparation of Isooctyl Cyanoacrylate

The isooctyl cyanoacrylate was prepared according to the preparation method of butyl lactyl cyanoacrylate, the feeding was as follows: isooctyl cyanoacetate (200 g, 1.01 mol, Tstachi (Shanghai) into Industrial Development Co., Ltd.), 1,2-dichloroethane (200 ml, Sinopharm Chemical Reagent Co., Ltd.), water solution of formaldehyde (36%, 78 g, 0.94 mol, Sinopharm Chemical Reagent Co., Ltd.), piperidine (1 mL, Sinopharm Chemical Reagent Co., Ltd.), dibutyl phthalate (150 mL, Sinopharm Chemical Reagent Co., Ltd.), hydroquinone (4 g, Sinopharm Chemical Reagent Co., Ltd.), p-toluenesulfonic acid (2 g, Sinopharm Chemical Reagent Co., Ltd.), and phosphorus pentoxide (4 g, Sinopharm Chemical Reagent Co., Ltd.), and then the pure isooctyl cyanoacrylate was obtained(123 g, 0.59 mol, yield 62.4%).

Preparation Example 5: Preparation of Ethoxy Ethyl Cyanoacrylate

The ethoxy ethyl cyanoacrylate was prepared according to the preparation method of butyl lactyl cyanoacrylate, the feeding was as follows: ethoxy ethyl cyanoacetate (200 g, 1.27 mol, Tstachi (Shanghai) into Industrial Development Co., Ltd.), 1,2-dichloroethane (200 ml, Sinopharm Chemical Reagent Co., Ltd.), water solution of formaldehyde (36%, 98 g, 1.18 mol, Sinopharm Chemical Reagent Co., Ltd.), piperidine(1 mL, Sinopharm Chemical Reagent Co., Ltd.), dibutyl phthalate (150 mL, Sinopharm Chemical Reagent Co., Ltd.), hydroquinone (4 g, Sinopharm Chemical Reagent Co., Ltd.), p-toluenesulfonic acid (2 g, Sinopharm Chemical Reagent Co., Ltd.), and phosphorus pentoxide (4 g, Sinopharm Chemical Reagent Co., Ltd.), and then the pure ethoxy ethyl cyanoacrylate was obtained((112 g, 0.66 mol, yield 56.1%).

Example 1

Preparation of Degradable Cyanoacrylate Medical Adhesive (Medical Adhesive 1)

1) The butyl cyanoacrylate (60 g, 0.39 mol, the preparation example 3), butyl lactyl cyanoacrylate (30 g, 0.13 mol, the preparation example 1), p-hydroxyanisole (45 mg, 500 ppm of total weight of cyanoacrylate medical adhesive, Aladdin reagent (Shanghai) Co., Ltd.) and butyl hydroxyanisole (BHA) (18 mg, 200 ppm of total weight of cyanoacrylate medical adhesive, Aladdin reagent (Shanghai) Co., Ltd.) as free radical polymerization inhibitors, p-toluenesulfonic acid (9 mg, 100 ppm of total weight of cyanoacrylate medical adhesive, Aladdin reagent (Shanghai) Co. Ltd.) as anion polymerization inhibitor and phytic acid (9 mg, 100 ppm of total weight of cyanoacrylate medical adhesive, Zhengzhou Yizhizhong chemicals Co., Ltd.) as natural antioxidant were weighed successively, and mixed evenly to obtain colorless liquid;

2) Sulfur dioxide (9 mg, 100 ppm of total weight of cyanoacrylate medical adhesive) as gas polymerization inhibitor was added to the colorless liquid obtained in step 1), the mixture was sealed well and stirred for 18 hours at room temperature.

3) Under the condition of local hundred class, the mixture obtained in step 2) was filtered by 0.22 μm PTFE filter membrane to remove bacteria, and sterile medical adhesive 1 was obtained, then sterile medical adhesive was filled into the sterile ampoule bottle, of which the filling volume was set to 0.5 mL, and the total filling amount was 100 ampoules.

Contrast Example 1

Degradable cyanoacrylate medical adhesive was prepared in the same preparation method of example 1 while without adding phytic acid.

Example 2

Preparation of Degradable Cyanoacrylate Medical Adhesive (Medical Adhesive 2)

1) The isooctyl cyanoacrylate (200 g, 0.96 mol, the preparation example 4), butyl lactyl cyanoacrylate (72 g, 0.32 mol, the preparation example 1), p-hydroxyanisole (136 mg, 500 ppm of total weight of cyanoacrylate medical adhesive, Aladdin reagent (Shanghai) Co., Ltd.) and butyl hydroxyanisole (BHA) (54 mg, 200 ppm of total weight of cyanoacrylate medical adhesive, Aladdin reagent (Shanghai) Co., Ltd.) as free radical polymerization inhibitors, and methanesulfonic acid (27 mg, 100 ppm of total weight of cyanoacrylate medical adhesive, Aladdin reagent (Shanghai) Co., Ltd.) as anion polymerization inhibitor were weighed successively and mixed fully, and sulfur dioxide (27 mg, 100 ppm of total weight of cyanoacrylate medical adhesive) as gas polymerization inhibitor was added, then the mixture was sealed well and stirred for 18 hours at room temperature to obtain the colorless liquid mixture.

2) The colorless liquid mixture obtained in step 1) was divided into 5 parts, the phytic acid of 2 mg (37 ppm of total weight of cyanoacrylate medical adhesive, Zhengzhou Yizhizhong chemicals Co., Ltd.), 3 mg (55 ppm of total weight of cyanoacrylate medical adhesive, Zhengzhou Yizhizhong chemicals Co., Ltd.), 6 mg (110 ppm of total weight of cyanoacrylate medical adhesive, Zhengzhou Yizhizhong chemicals Co., Ltd.), 16 mg (294 ppm of total weight of cyanoacrylate medical adhesive, Zhengzhou Yizhizhong chemicals Co., Ltd.) and 54 mg (993 ppm of total weight of cyanoacrylate medical adhesive, Zhengzhou Yizhizhong chemicals Co., Ltd.) were added into 5 samples respectively and fully mixed to obtain colorless liquids.

3) Under the condition of local hundred class, the colorless liquids obtained in step 2) were filtered by 0.22 μm PTFE filter membrane to remove bacteria, and sterile medical adhesives were obtained respectively, which were numbered as medical adhesive 2-1, medical adhesive 2-2, medical adhesive 2-3, medical adhesive 2-4 and medical adhesive 2-5, then these medical adhesives were filled into the sterile ampoule bottles, of which the filling volume was set to 0.5 mL, and the total filling amount was 80 ampoules.

The main performance indicators of the medical adhesive 2-1, medical adhesive 2-2, medical adhesive 2-3, medical adhesive 2-4 and medical adhesive 2-5 were tested according to the test items and detection methods respectively, and the results were shown in Table 2.

TABLE 1

The Influence of the phytic acid amount on the performance indicators of medical adhesive

| Test items | Samples | | | | | | |
|---|---|---|---|---|---|---|---|
| | Medical adhesive 1 | Medical adhesive 2-1 | Medical adhesive 2-2 | Medical adhesive 2-3 | Medical adhesive 2-4 | Medical adhesive 2-5 | Contrast example 1 |
| Shelf life ($TIME_{22°C}$) (day) | 730 | 210 | 420 | 730 | 730 | 730 | 70 |
| Curing time (s) | 8 | 8 | 8 | 8 | 8 | 8 | 8 |

TABLE 1-continued

The Influence of the phytic acid amount on the performance indicators of medical adhesive

| | | Samples | | | | | | |
|---|---|---|---|---|---|---|---|---|
| Test items | | Medical adhesive 1 | Medical adhesive 2-1 | Medical adhesive 2-2 | Medical adhesive 2-3 | Medical adhesive 2-4 | Medical adhesive 2-5 | Contrast example 1 |
| Bonding strength | Strength in lap shear by tension loading (N/cm) | 0.12 | 0.10 | 0.10 | 0.12 | 0.09 | 0.07 | 0.10 |
| | Strength in T-peel by tension loading (N/cm) | 2.2 | 2.1 | 2.1 | 2.1 | 1.8 | 1.8 | 2.1 |
| | Tension strength (MPa) | 0.13 | 0.13 | 0.12 | 0.13 | 0.11 | 0.10 | 0.13 |
| | Wound closure strength (N) | 16 | 15 | 15 | 16 | 14 | 12 | 15 |
| In vitro degradation time ($TIVD_{37°C.}$) (day) | | 140 | 140 | 140 | 140 | 140 | 140 | 140 |

Example 3

Preparation of Degradable Cyanoacrylate Medical Adhesive (Medical Adhesive 3)

1) The isooctyl cyanoacrylate (50 g, 0.24 mol, the preparation example 4), isooctyl lactyl cyanoacrylate (22 g, 0.08 mol, the preparation example 2), hydroquinone (36 mg, 500 ppm of total weight of cyanoacrylate medical adhesive, Aladdin reagent (Shanghai) Co., Ltd.) and 2,6-di-tert-butyl-4-methylphenol (BHT) (14.5 mg, 200 ppm of total weight of cyanoacrylate medical adhesive, Aladdin reagent (Shanghai) Co., Ltd.) as free radical polymerization inhibitors, and p-toluenesulfonic acid (8 mg, 110 ppm of total weight of cyanoacrylate medical adhesive, Aladdin reagent (Shanghai) Co., Ltd.) as anion polymerization inhibitor were weighed successively and mixed fully, then citric acid (8 mg, 110 ppm of total weight of cyanoacrylate medical adhesive, Zhengzhou Yizhizhong chemicals Co., Ltd.) as natural antioxidant was added, and the mixture was fully mixed to obtain colorless liquid;

2) Boron trifluoride (8 mg, 110 ppm of total weight of cyanoacrylate medical adhesive) as gas polymerization inhibitor was added to the colorless liquid obtained in step 1), then the mixture was sealed well and stirred for 18 hours at room temperature.

3) Under the condition of local hundred class, the colorless liquid obtained in step 2) was filtered by 0.22 μm PTFE filter membrane to remove bacteria, then sterile medical adhesive 3 was obtained and filled into the sterile ampoule bottle, of which the filling volume was set to 0.5 mL, and the total filling amount was 100 ampoules.

Example 4

Preparation of Degradable Cyanoacrylate Medical Adhesive (Medical Adhesive 4)

1) The ethoxy ethyl cyanoacrylate (68 g, 0.4 mol, the preparation example 5), the butyl lactyl cyanoacrylate of preparation example 1 above (32 g, 0.14 mol, the preparation example 1), p-dimethoxybenzene (50 mg, 500 ppm of total weight of cyanoacrylate medical adhesive, Aladdin reagent (Shanghai) Co., Ltd.) and tert-butylhydroquinon (TBHQ) (20 mg, 200 ppm of total weight of cyanoacrylate medical adhesive, Aladdin reagent (Shanghai) Co., Ltd.) as free radical polymerization inhibitors, methanesulfonic acid (10 mg, 100 ppm of total weight of cyanoacrylate medical adhesive, Aladdin reagent (Shanghai) Co., Ltd.) as anion polymerization inhibitor, and ascorbic acid (10 mg, 100 ppm of total weight of cyanoacrylate medical adhesive, Zhengzhou Yizhizhong chemicals Co., Ltd.) as natural antioxidant were weighed successively and fully mixed to obtain colorless liquid;

2) Sulfur dioxide (10 mg, 100 ppm of total weight of cyanoacrylate medical adhesive) as gas polymerization inhibitor was added into the colorless liquid obtained in step 1), then the mixture was sealed well and stirred for 18 hours at room temperature.

3) Under the condition of local hundred class, the colorless liquid obtained in step 2) was filtered by 0.22 μm PTFE filter membrane to remove bacteria, and sterile medical adhesive 4 was obtained and filled into the sterile ampoule bottle, of which the filling volume was set to 0.5 mL, and the total filling amount was 100 ampoules.

Example 5

Preparation of Degradable Cyanoacrylate Medical Adhesive (Medical Adhesive 5)

1) The n-butyl cyanoacrylate (31 g, 0.20 mol, the preparation example 3), ethoxy ethyl cyanoacrylate (34 g, 0.20 mol, the preparation example 5), butyl lactyl cyanoacrylate (25 g, 0.111 mol, the preparation example 1), p-dimethoxybenzene (45 mg, 500 ppm of total weight of cyanoacrylate medical adhesive, Aladdin reagent (Shanghai) Co., Ltd.), and 2,5-di-tert-butylhydroquinone (DBHQ) (18 mg, 200 ppm of total weight of cyanoacrylate medical adhesive, Aladdin reagent (Shanghai) Co., Ltd.) as free radical polymerization inhibitors, perchloric acid (9 mg, 100 ppm of total weight of cyanoacrylate medical adhesive, Aladdin reagent (Shanghai) Co., Ltd.) as anion polymerization inhibitor, and phytic acid (10 mg, 110 ppm of total weight of cyanoacrylate medical adhesive, Zhengzhou Yizhizhong chemicals Co., Ltd.) as natural antioxidant were weighed successively and fully mixed to obtain colorless liquid;

2) Sulfur dioxide (10 mg, 110 ppm of total weight of cyanoacrylate medical adhesive) as gas polymerization inhibitor was added into the colorless liquid obtained in step 1), then the mixture was sealed well and stirred for 18 hours at room temperature.

3) Under the condition of local hundred class, the colorless liquid obtained in step 2) was filtered by 0.22 μm PTFE filter membrane to remove bacteria, then sterile medical adhesive 5 was obtained and filled into the sterile ampoule bottle, of which the filling volume was set to 0.5 mL, and the total filling amount was 100 ampoules.

Example 6

Preparation of Degradable Cyanoacrylate Medical Adhesive (Medical Adhesive 6)

1) The n-butyl cyanoacrylate (160 g, 1.04 mol, the preparation example 3), the butyl lactyl cyanoacrylate of the preparation example 1 above (80 g, 0.35 mol, the preparation example 1), p-hydroxyanisole (120 mg, 500 ppm of total weight of cyanoacrylate medical adhesive, Aladdin reagent (Shanghai) Co., Ltd.) and butyl hydroxyanisole (BHA) (48 mg, 200 ppm of total weight of cyanoacrylate medical adhesive, Aladdin reagent (Shanghai) Co., Ltd) as free radical polymerization inhibitors, methanesulfonic acid (24 mg, 100 ppm of total weight of cyanoacrylate medical adhesive, Aladdin reagent (Shanghai) Co., Ltd.) as anion polymerization inhibitor, and phytic acid (24 mg, 100 ppm of total weight of cyanoacrylate medical adhesive, Zhengzhou Yizhizhong chemicals Co., Ltd.) as natural antioxidant were weighed successively and fully mixed to obtain colorless liquid, then sulfur dioxide (24 mg, 100 ppm of total weight of cyanoacrylate medical adhesive) as gas polymerization inhibitor was added to the colorless liquid, then the mixture was sealed well and stirred for 18 hours at room temperature to obtain colorless liquid.

2) Medical adhesive obtained in step 1) was divided uniformly into 4 parts, polylactic acids (PLA, molecular weight was 20000, Shenzhen Boli biological material Co., Ltd.) 2.4 g (cyanoacrylate compositions (A): degradable molecular material (B)=100:1), 4.8 g (cyanoacrylate compositions (A): the degradable molecular material (B)=50:1), 12 g (cyanoacrylate compositions (A): the degradable molecular material (B)=20:1) and 24 g (cyanoacrylate compositions (A): the degradable molecular material (B)=10:1) were added into 4 samples respectively and fully mixed to obtain colorless viscous liquids.

3) Under the condition of local hundred class, the colorless viscous liquids obtained in step 2) were filtered by 0.22 μm PTFE filter membrane to remove bacteria, and sterile medical adhesives were obtained respectively, which were numbered as medical adhesive 6-1, medical adhesive 6-2, medical adhesive 6-3, and medical adhesive 6-4, then these medical adhesives were filled into the sterile ampoule bottles, of which the filling volume was set to 0.5 mL, and the total filling amount was 100 ampoules.

The properties of the samples prepared above were compared with those of the medical adhesive 1 obtained in the example 1, and showed in the next table.

Example 7

Preparation of Degradable Cyanoacrylate Medical Adhesive (Medical Adhesive 7)

1) The n-butyl cyanoacrylate (31 g, 0.20 mol, the preparation example 3), ethoxy ethyl cyanoacrylate (34 g, 0.20 mol, the preparation example 5), butyl lactyl cyanoacrylate (25 g, 0.111 mol, the preparation example 1), p-dimethoxybenzene (45 mg, 500 ppm of total weight of cyanoacrylate medical adhesive, Aladdin reagent (Shanghai) Co., Ltd.) and 2,5-di-tert-butylhydroquinone (DBHQ) (18 mg, 200 ppm of total weight of cyanoacrylate medical adhesive, Aladdin reagent (Shanghai) Co., Ltd.) as free radical polymerization inhibitors, methanesulfonic acid (9 mg, 100 ppm of total weight of cyanoacrylate medical adhesive, Aladdin reagent (Shanghai) Co., Ltd.) as anion polymerization inhibitor, copolymer of lactic acid and lactide (PLGA, 4.5 g, cyanoacrylate compositions (A): degradable polymer (B)=20:1, molecular weight was 20000, Shenzhen Boli biological material Co., Ltd.), and phytic acid (10 mg, 110 ppm of total weight of cyanoacrylate medical adhesive, Zhengzhou Yizhizhong chemicals Co., Ltd.) as natural antioxidant were weighed successively and fully mixed, to obtain colorless viscous liquid.

2) Sulfur dioxide (10 mg, 105 ppm of total weight of cyanoacrylate medical adhesive) as gas polymerization inhibitor was added to the colorless viscous liquid obtained in step 1), then the mixture was sealed well and stirred for 18 hours at room temperature.

3) Under the condition of local hundred class, the colorless viscous liquid obtained in step 2) was filtered by 0.22 μm PTFE filter membrane to remove bacteria, then sterile medical adhesive 7 was obtained and filled into the sterile ampoule bottle, of which the filling volume was set to 0.5 mL, and the total filling amount was 100 ampoules.

Contrast Example 2

Degradable cyanoacrylate medical adhesive was prepared in the same preparation method of example 7 while without adding phytic acid.

TABLE 2

The research and main performance indicator detections of degradable cyanoacrylate medical adhesive

| | Test items | Medical adhesive 6-1 | Medical adhesive 6-2 | Medical adhesive 6-3 | Medical adhesive 6-4 | Medical adhesive 1 |
|---|---|---|---|---|---|---|
| | Shelf life ($TIME_{22°C}$) (day) | 730 | 730 | 730 | 730 | 730 |
| | Curing time (s) | 8 | 8 | 9 | 10 | 8 |
| Bonding strength | Strength in lap shear by tension loading (N/cm) | 0.12 | 0.10 | 0.10 | 0.09 | 0.12 |
| | Strength in T-peel by tension loading (N/cm) | 2.2 | 2.0 | 1.8 | 1.6 | 2.2 |
| | Tension strength (MPa) | 0.12 | 0.12 | 0.11 | 0.10 | 0.13 |
| | Wound closure strength (N) | 15 | 14 | 14 | 12 | 16 |
| | In vitro degradation time ($TIVD_{37°C}$) (day) | 126 | 105 | 98 | 84 | 140 |

TABLE 3

The main performance indicator comparisons of cyanoacrylate medical adhesive and contrast example prepared in the disclosure

| Test items | | Medical adhesive 1 | Medical adhesive 2-3 | Medical adhesive 3 | Medical adhesive 4 | Medical adhesive 5 | Medical adhesive 6-2 | Medical adhesive 7 | Contrast example 1 | Contrast example 2 |
|---|---|---|---|---|---|---|---|---|---|---|
| Shelf life ($TIME_{22°C.}$) (day) | | 730 | 730 | 420 | 420 | 730 | 730 | 730 | 70 | 70 |
| Curing time (s) | | 8 | 8 | 10 | 10 | 10 | 8 | 15 | 8 | 15 |
| Bonding strength | Strength in lap shear by tension loading (N/cm) | 0.12 | 0.13 | 0.10 | 0.12 | 0.12 | 0.10 | 0.09 | 0.12 | 0.09 |
| | Strength in T-peel by tension loading (N/cm) | 2.1 | 2.1 | 2.0 | 2.0 | 2.1 | 2.0 | 1.6 | 2.1 | 1.6 |
| | Tension strength (MPa) | 0.12 | 0.13 | 0.11 | 0.12 | 0.12 | 0.12 | 0.08 | 0.12 | 0.08 |
| | Wound closure strength (N) | 16 | 16 | 15 | 15 | 14 | 14 | 12 | 16 | 12 |
| In vitro degradation time ($TIVD_{37°C.}$) (day) | | 140 | 140 | 140 | 140 | 140 | 105 | 84 | 140 | 84 |

As table 3 showed, the traditional cyanoacrylate stabilizer system (the stabilizer was composed of free radical polymerization inhibitor, anion polymerization inhibitor and gas polymerization inhibitor) did not have stable effect on degradable cyanoacrylate medical adhesive, such as, the contrast examples 1 and 2, while after a lot of experiments, it was surprising to find that adding trace natural antioxidant into the traditional stabilizer system could significantly prolong the shelf life of degradable cyanoacrylate medical adhesive, of which the shelf life reached more than 730 days (two years), but the shelf life of the contrast example without natural antioxidant was less than 70 days, that is, in the present examples, synergistic effect was produced by adding the natural antioxidant which worked with the existing cyanoacrylate stabilizer and greatly improved the stability of the cyanoacrylate medical adhesive in the present disclosure.

The table 3 also showed that, phytic acid, citric acid and ascorbic acid could all produce synergistic effect with existing cyanoacrylate stabilizer system, and the shelf life of degradable cyanoacrylate medical adhesives which comprised the natural antioxidant was respectively 730 days, 420 days and 420 days, in which the synergistic effect of phytic acid was the best.

The table 3 also showed, adding the degradable polymer, such as PLA and PLGA etc., did not affect the stability of degradable cyanoacrylate medical adhesive, but can significantly improve the degradation rate of the product, and adding PLA and PLGA also affected the bonding rate and bonding strength of the product, so it can ensure not only faster degradation rate of medical adhesive, but also the bonding rate and bonding strength of medical adhesive to meet the need of medical use by controlling the amount of PLA and PLGA, such as controlling the ratio of cyanoacrylate composition (A): degradable polymer (B) as 20:1.

As table 1 showed, the amount of phytic acid was also a factor which affected synergistic effect, when the amount of phytic acid was 2 mg (about 37 ppm of total weight of cyanoacrylate medical adhesive), shelf life of medical adhesive 2-1 could reach 210 days or so, which was obviously improved compared with medical adhesive 1 without phytic acid, so it could be seen that even trace phytic acid could produce a good synergistic effect; and if the amount of phytic acid continued to be increased and reached 3 mg (55 ppm of total weight of cyanoacrylate medical adhesive), the shelf life of medical adhesive 2-2 increased to 420 days or so; when the amount of phytic acid reached 6 mg (110 ppm of total weight of cyanoacrylate medical adhesive), the shelf life of the degradable cyanoacrylate medical adhesive reached 730 days or so, which can meet the demand of the products. The inventor also tried to continue to increase the amount of phytic acid, for example, when the phytic acid amount reached 18 mg (300 ppm of total weight of cyanoacrylate medical adhesive) and 54 mg (993 ppm of total weight of cyanoacrylate medical adhesive), the shelf life of products could still meet the requirements of medical adhesive well, but when the amount of phytic acid reached 1000 ppm of total weight of cyanoacrylate medical adhesive, if the amount of phytic acid was still increased, main technical indicators of the product, such as curing time and bonding strength, decreased significantly, so the amount 30-1000 ppm of phytic acid could effectively extend the shelf life of the product, of which 100-300 ppm was the best.

As table 2 showed, adding polylactic acid could effectively shorten in vitro degradation time, and with the increasing amount of polylactic acid, the degradation time was shortened continually, but the curing time and bonding strength of products decreased slowly, when the amount of polylactic acid was as cyanoacrylate composition (A): degradable polymer (B)=100:1, the main technical indicators of cyanoacrylate medical adhesive did not appear an obvious decrease; when the amount of polylactic acid was as cyanoacrylate composition (A): degradable polymer (B)=50:1, the main technical indicators of cyanoacrylate medical adhesive appeared a decrease, but still met the clinical use well. When the amount of polylactic acid was as cyanoacrylate composition (A): degradable polymer (B)=20:1, although the main technical indicators of cyanoacrylate medical adhesive still met the clinical use well, the viscosity of the products became obviously larger, which was inconvenient to sterilization. When the amount of polylactic acid was as cyanoacrylate composition (A):

degradable polymer (B)=10:1, the main product performance indicators all substantially declined, at the same time the viscosity of the products increased substantially, and post processing became extremely difficult. Also because the polylactic acid was expensive, it substantially increased the cost of products. So it could be concluded that the mass ratio of cyanoacrylate composition to degradable polymer was preferably 100:1-20:1.

The invention claimed is:

1. Cyanoacrylate medical adhesive, wherein the medical adhesive is prepared by raw materials comprising the following components: a cyanoacrylate composition (A); and a composite stabilizer (C);

wherein the cyanoacrylate composition (A) comprises the following components:

A1: a alkyl cyanoacrylate compound and/or alkoxy cyanoacrylate compound, wherein the alkyl cyanoacrylate compound comprises one or more compounds of methyl cyanoacrylate, ethyl cyanoacrylate, isobutyl cyanoacrylate, n-butyl cyanoacrylate, n-octyl cyanoacrylate, or isooctyl cyanoacrylate; the alkoxy cyanoacrylate compound comprises one or more compounds of methoxy methyl cyanoacrylate, methoxy ethyl cyanoacrylate, methoxy butyl cyanoacrylate, methoxy octyl cyanoacrylate, ethoxy methyl cyanoacrylate, ethoxy ethyl cyanoacrylate, ethoxy butyl cyanoacrylate, or ethoxy octyl cyanoacrylate; and A2: a lactyl cyanoacrylate compound, wherein the lactyl cyanoacrylate compound comprises one or more compounds of methyl lactyl cyanoacrylate, ethyl lactyl cyanoacrylate, propyl lactyl cyanoacrylate, butyl lactyl cyanoacrylate, pentyl lactyl cyanoacrylate, hexyl lactyl cyanoacrylate or isooctyl lactyl cyanoacrylate;

wherein the composite stabilizer (C) comprises at least the following components:

C1: an anion polymerization inhibitor, wherein the anion polymerization inhibitor comprises a strong acid substance selected from perchloric acid, permanganic acid, sulfuric acid, methanesulfonic acid, p-toluene sulfonic acid, hydrofluoric acid, sulfonic acid or mixtures thereof;

C2: a gas polymerization inhibitor, wherein the gas polymerization inhibitor is acidic gas selected from hydrogen chloride, boron trifluoride, sulfur dioxide, nitrogen dioxide or mixtures thereof;

C3: a free radical polymerization inhibitor, which comprises a quinone polymerization inhibitor with smaller steric hindrance and a quinone polymerization inhibitor with larger steric hindrance; the quinone polymerization inhibitor with smaller steric hindrance comprises one or more compounds of hydroquinone, p-hydroxyanisole and p-dimethoxybenzene; the quinone polymerization inhibitor with larger steric hindrance comprises one or more compounds of butyl hydroxyanisole (BHA), 2,6-di-tert-butyl-4-methylphenol(BHT), tert-butyl hydroquinone(TBHQ), 2,5-di-tert-butyl hydroquinone(DBHQ), p-tert-butylcatechol (TBC), 1,1-diphenyl-2-trinitrophenyl hydrazine(DPPH);

C4: a natural antioxidant, wherein the natural antioxidant is selected from phytic acid;

wherein molar ratio of the alkyl cyanoacrylate compound and/or the alkoxy cyanoacrylate compound (A1) to the lactyl cyanoacrylate compound (A2) is A1:A2=10:1-1:1; amount of the anion polymerization inhibitor is 30-1000 ppm of total weight of cyanoacrylate medical adhesive, amount of the gas polymerization inhibitor is 20-500 ppm of total weight of cyanoacrylate medical adhesive, amount of the quinone polymerization inhibitor with smaller steric hindrance is 50-2000 ppm of total weight of cyanoacrylate medical adhesive, amount of the quinone polymerization inhibitor with larger steric hindrance is 50-1000 ppm of total weight of cyanoacrylate medical adhesive, amount of the natural antioxidant is 30-1000 ppm of total weight of cyanoacrylate medical adhesive.

2. The cyanoacrylate medical adhesive of claim 1, wherein the cyanoacrylate medical adhesive also comprises degradable polymer (B), the degradable polymer is at least one kind selected from polylactic acid (PLA), polycaprolactone (PCL), polylactide (PGA), copolymer of lactic acid and caprolactone (PLCL) and copolymer of lactic acid and lactide (PLGA).

3. The cyanoacrylate medical adhesive of claim 1, wherein the alkyl cyanoacrylate compound is n-butyl cyanoacrylate or isooctyl cyanoacrylate; the alkoxy cyanoacrylate compound is ethoxy ethyl cyanoacrylate; the lactyl cyanoacrylate compound is butyl lactyl cyanoacrylate (BLCA) or isooctyl lactyl cyanoacrylate.

4. The cyanoacrylate medical adhesive of claim 2, wherein the degradable polymer (B) is polylactic acid (PLA) or copolymer of lactic acid and lactide (PLGA).

5. The cyanoacrylate medical adhesive of claim 1, wherein the anion polymerization inhibitor is methanesulfonic acid or p-toluene sulfonic acid; the gas polymerization inhibitor is sulfur dioxide or boron trifluoride; the quinone polymerization inhibitor with smaller steric hindrance is p-hydroxyanisole; the quinone polymerization inhibitor with larger steric hindrance is butyl hydroxyanisole (BHA) or 2,5-di-tert-butyl hydroquinone (DBHQ).

6. The cyanoacrylate medical adhesive of claim 2, wherein the mass ratio of cyanoacrylate composition (A) to the degradable polymer (B) is A:B=100:1-20:1.

7. The cyanoacrylate medical adhesive of claim 1, wherein amount of the anion polymerization inhibitor is 50-500 ppm of total weight of cyanoacrylate medical adhesive.

8. A method for preparing the cyanoacrylate medical adhesive of claim 1, comprising the following steps:
1) weighting successively alkyl cyanoacrylate and/or alkoxy cyanoacrylate, lactyl cyanoacrylate, free radical polymerization inhibitor, anion polymerization inhibitor and natural antioxidant, mixing evenly to obtain colorless liquid;
2) adding gas polymerization inhibitor to the colorless liquid obtained in step 1), then sealing well, and stirring for 12-24 hours at room temperature; and
3) under the condition of local laminar flow, filtering the mixture obtained in step 2 to remove bacteria and obtain sterile degradable cyanoacrylate medical adhesive.

9. The cyanoacrylate medical adhesive of claim 7, wherein amount of the anion polymerization inhibitor is 50-200 ppm of total weight of cyanoacrylate medical adhesive.

10. The cyanoacrylate medical adhesive of claim 1, wherein amount of the gas polymerization inhibitor is 30-300 ppm of total weight of cyanoacrylate medical adhesive.

11. The cyanoacrylate medical adhesive of claim 10, wherein amount of the gas polymerization inhibitor is 50-200 ppm of total weight of cyanoacrylate medical adhesive.

12. The cyanoacrylate medical adhesive of claim 1, wherein amount of the quinone polymerization inhibitor with smaller steric hindrance is 100-1000 ppm of total weight of cyanoacrylate medical adhesive.

13. The cyanoacrylate medical adhesive of claim 12, wherein amount of the quinone polymerization inhibitor with smaller steric hindrance is 300-800 ppm of total weight of cyanoacrylate medical adhesive.

14. The cyanoacrylate medical adhesive of claim 1, wherein amount of the quinone polymerization inhibitor with larger steric hindrance is 100-800 ppm of total weight of cyanoacrylate medical adhesive.

15. The cyanoacrylate medical adhesive of claim 14, wherein amount of the quinone polymerization inhibitor with larger steric hindrance is 200-500 ppm of total weight of cyanoacrylate medical adhesive.

16. The cyanoacrylate medical adhesive of claim 1, wherein amount of the natural antioxidant is 50-500 ppm of total weight of cyanoacrylate medical adhesive.

17. The cyanoacrylate medical adhesive of claim 16, wherein amount of the natural antioxidant is 100-300 ppm of total weight of cyanoacrylate medical adhesive.

18. A method for preparing the cyanoacrylate medical adhesive of claim 8, wherein the step 1) also comprises a step of adding a degradable polymer (B).

19. A method of hemostasis, comprising the step of administering effective dose of cyanoacrylate medical adhesive of claim 1 to a subject with hemostasis needs.

* * * * *